United States Patent
Munro (10) Patent No.: US 8,186,351 B2
(45) Date of Patent: May 29, 2012

(54) REACTIVE MEDICAL DEVICES

(75) Inventor: Andrew Munro, Livermore, CA (US)

(73) Assignee: Nellcor Puritan Bennett LLC, Boulder, CA (US)

( * ) Notice: Subject to any disclaimer, the term of this patent is extended or adjusted under 35 U.S.C. 154(b) by 821 days.

(21) Appl. No.: 12/344,814

(22) Filed: Dec. 29, 2008

(65) Prior Publication Data
US 2009/0165794 A1   Jul. 2, 2009

Related U.S. Application Data

(60) Provisional application No. 61/018,189, filed on Dec. 31, 2007.

(51) Int. Cl.
*A61M 16/00* (2006.01)
*A62B 9/06* (2006.01)

(52) U.S. Cl. .............................. 128/207.15; 128/207.14

(58) Field of Classification Search ............. 601/200.24, 601/200.26, 207.14–207.18; 604/96.01; A61M 16/00; A62B 9/06
See application file for complete search history.

(56) References Cited

U.S. PATENT DOCUMENTS

| | | | |
|---|---|---|---|
| 6,607,542 B1 * | 8/2003 | Wild ............................. | 606/157 |
| 7,096,868 B2 | 8/2006 | Tateo et al. | |
| 2004/0220534 A1 | 11/2004 | Martens et al. | |
| 2006/0118121 A1 | 6/2006 | Martens et al. | |
| 2006/0118122 A1 | 6/2006 | Martens et al. | |
| 2007/0289596 A1 | 12/2007 | Campbell et al. | |
| 2007/0290167 A1 * | 12/2007 | Mather et al. ............ | 252/299.01 |
| 2007/0295336 A1 | 12/2007 | Nelson et al. | |
| 2007/0295337 A1 | 12/2007 | Nelson et al. | |
| 2007/0296125 A1 | 12/2007 | Colburn et al. | |
| 2008/0000482 A1 | 1/2008 | Maguire et al. | |
| 2008/0072905 A1 | 3/2008 | Baker et al. | |
| 2008/0073231 A1 | 3/2008 | Clayton et al. | |
| 2008/0076977 A1 | 3/2008 | Mannheimer et al. | |
| 2008/0078399 A1 | 4/2008 | O'Neil et al. | |
| 2008/0078400 A1 | 4/2008 | Martens et al. | |
| 2008/0078401 A1 | 4/2008 | O'Neil et al. | |
| 2008/0078403 A1 | 4/2008 | Clayton | |
| 2008/0078404 A1 | 4/2008 | Martens | |
| 2008/0078405 A1 | 4/2008 | Crumback et al. | |
| 2008/0078406 A1 | 4/2008 | Clayton et al. | |
| 2008/0110468 A1 | 5/2008 | Nelson et al. | |
| 2008/0142016 A1 | 6/2008 | Colburn et al. | |
| 2008/0210243 A1 | 9/2008 | Clayton et al. | |
| 2008/0215034 A1 | 9/2008 | Clayton et al. | |
| 2011/0046669 A1* | 2/2011 | Goraltchouk et al. ........ | 606/228 |

OTHER PUBLICATIONS

Camacho-Lopez, Miguel, et al., Fast Liquid-Crystal Elastomer Swims Into the Dark, Letters, Nature Materials, vol. 3, May 2004, www.nature.com/naturematerials.

Courty, S., et al., Nematic elastomers with aligned carbon nanotubes: New electromechanical actuators, Europhysics Letters, Europhys. Lett., 64 (5), pp. 654-660 (2003).

Dullenkopf, et al., "Fluid leakage past tracheal tube cuffs: evaluation on the new Microcuff endotracheal tube," Intensive Care Medicine, (2003) vol. 29, pp. 1849-1853.

(Continued)

*Primary Examiner* — LoAn Thanh
*Assistant Examiner* — Oren Ginsberg
(74) *Attorney, Agent, or Firm* — Fletcher Yoder (57) ABSTRACT

A tracheal tube comprising a nematic polymer or nematic elastomer, wherein an outer diameter of the tracheal tube changes in size in response to exposure of the tracheal tube to light or heat.

20 Claims, 11 Drawing Sheets

OTHER PUBLICATIONS

Finkelmann, H., et al., A New Opto-Mechanical Effect in Solids, vol. 87, #1, Jul. 2, 2001, The American Physical Society, Physical Review Letters.

Graham, Sarah, et al., Scientists Use Light to Make Polymers Change Shape and Size, Material Science, Jul. 3, 2001.

Sartomer Application Bulletin; Functional Acrylic Monomers as Modifiers for PVC Plastisol Formulations.

Tecogel Brochure Page, Noveon Thermedics Polymer Products, Oct. 2003.

Warner, Mark, et al., A Bird's Eye View of Liquid Crystal Elastomers, pp. 1-6, Book, Liquid Crystal Elastomers, Cavendish Laboratory, University of Cambridge, 2003.

* cited by examiner

FIG. 12

REACTIVE MEDICAL DEVICES

RELATED APPLICATION

This application claims priority from U.S. Patent Application Ser. No. 61/018,189 which was filed Dec. 31, 2007, and is incorporated herein by reference in its entirety.

BACKGROUND

The present disclosure relates to medical devices, and more particularly, to airway products, such as tracheal tubes.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, a tube or other medical device may be used to control the flow of air, food, fluids, or other substances into and/or out of the patient. For example, medical devices, such as tracheal tubes, may be used to control the flow of one or more substances into or out of a patient. In many instances, it is desirable to provide a seat between the outside of the tube or device and the interior of the passage in which the tube or device is inserted. In this way, substances can only flow through the passage via the tube or other medical device, allowing a medical practitioner to maintain control over the type and amount of substances flowing into and out of the patient.

Tracheal tubes may be used to control the flow of air or other gases through a patient's trachea. Such tracheal tubes may include endotracheal tubes and tracheostomy tubes. To seal these types of tracheal tubes, inflatable cuffs are sometimes associated with these tubes. When inflated, these cuffs generally expand into the surrounding trachea to seal the tracheal passage around the circumference of the tube. A high-quality seal against the tracheal passageway allows a ventilator to perform efficiently.

Generally, endotracheal tubes are available in a subset of sizes from which doctors may select the closest approximate size for a particular patient. The difference in tube sizes may generally reflect both differences in the length of the tube as well as different tube diameters. In particular, doctors may wish to select an endotracheal tube with an appropriate diameter in order to allow the tube to be easily inserted into the patient while providing the largest possible airway path for respiratory gases. For example, an endotracheal tube with too small a tube diameter may be associated with an increased work of breathing for the patient. Conversely, an endotracheal tube with too large a tube diameter presents certain disadvantages. For example, if the outer diameter of the endotracheal tube is too large, it can become difficult to navigate through the larynx and trachea. Thus, too large an endotracheal tube may increase the time it takes to intubate the patient. Also, a large endotracheal tube can prove somewhat uncomfortable for the patient. For instance, irritation of the tracheal walls can result from increased contact with the endotracheal tube.

SUMMARY

Certain aspects commensurate in scope with the originally claimed disclosure are set forth below. It should be understood that these aspects are presented merely to provide the reader with a brief summary of certain forms the disclosure might take and that these aspects are not intended to limit the scope of the disclosure. Indeed, the disclosure may encompass a variety of aspects that may not be set forth below.

There is provided a tracheal tube that incorporates a nematic polymer or nematic elastomer, wherein an outer diameter of the tracheal tube changes in size in response to exposure of the tracheal tube to an active light source or an active heat source.

There is provided a tracheal tube constructed of a nematic polymer incorporating a dye. The dye undergoes isomerization upon exposure to a light source or a heat source, wherein isomerization of the dye disrupts a nematic order of the nematic polymer.

There is provided a tracheal tube system including an energy source and a tracheal tube constructed of a nematic polymer or nematic elastomer. An outer diameter of the tracheal tube changes in size in response to exposure to the energy source when the energy source is active.

There is provided a method of treating a patient, including: activating an energy source to contract a tracheal tube; inserting the tracheal tube into a passageway of the patient; and deactivating the energy source to expand the tracheal tube to substantially seal an outer surface of the tracheal tube against the passageway of the patient.

There is provided a method of treating a patient including: deactivating an energy source to contract a tracheal tube; inserting the tracheal tube into a passageway of the patient; and activating the energy source to expand the tracheal tube to substantially seal an outer surface of the tracheal tube against the passageway of the patient.

There is provided a method of treating a patient including: exposing a tracheal tube to light having a wavelength in a first wavelength range to contract the tracheal tube; inserting the tracheal tube into a passageway of the patient; and exposing the tracheal tube to light having a wavelength in a second wavelength range to expand the tracheal tube to substantially seal an outer surface of the tracheal tube against the passageway of the patient.

BRIEF DESCRIPTION OF THE DRAWINGS

Advantages of the disclosure may become apparent upon reading the following detailed description and upon reference to the drawings in which.

DETAILED DESCRIPTION OF SPECIFIC EMBODIMENTS

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

It is desirable to provide an endotracheal tube or other medical device which may substantially seal the passage in which the tube is inserted so that mechanical ventilation can be used to introduce air, oxygen, or medications into the body (e.g., lungs). In accordance with the present disclosure, an endotracheal tube is constructed of or incorporates a plastic that responds to either light and/or heat to resize. Examples of such plastics include nematic elastomers, which change shape based on the presence or absence of light. The changing of shape (e.g., diameter) of the endotracheal tube in response to light and/or heat may facilitate the insertion, sealing, and removal of the tube in the patient.

Figure 1:
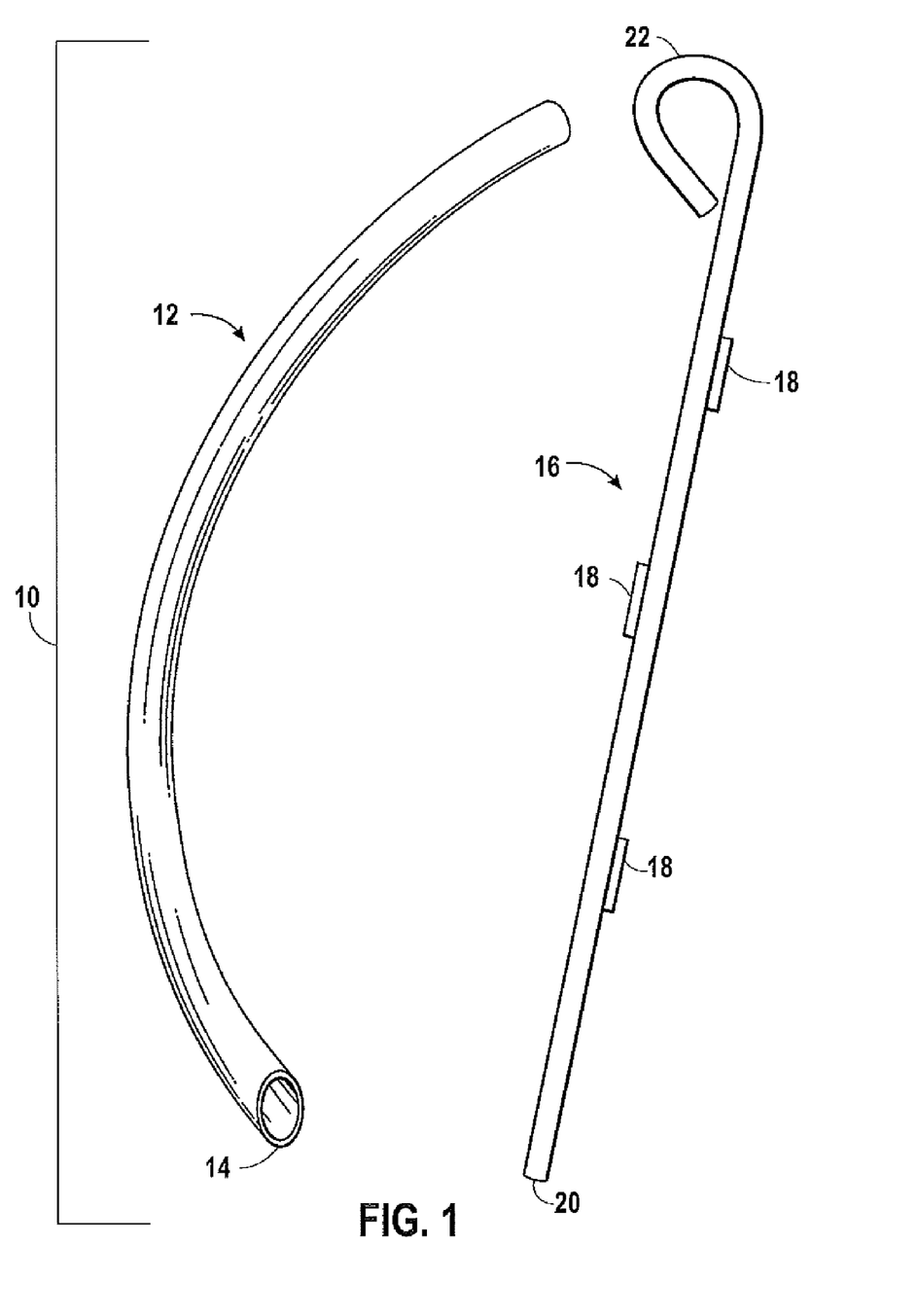
FIG. 1 illustrates an endotracheal system in accordance with an embodiment of the present disclosure.
Figure 2:
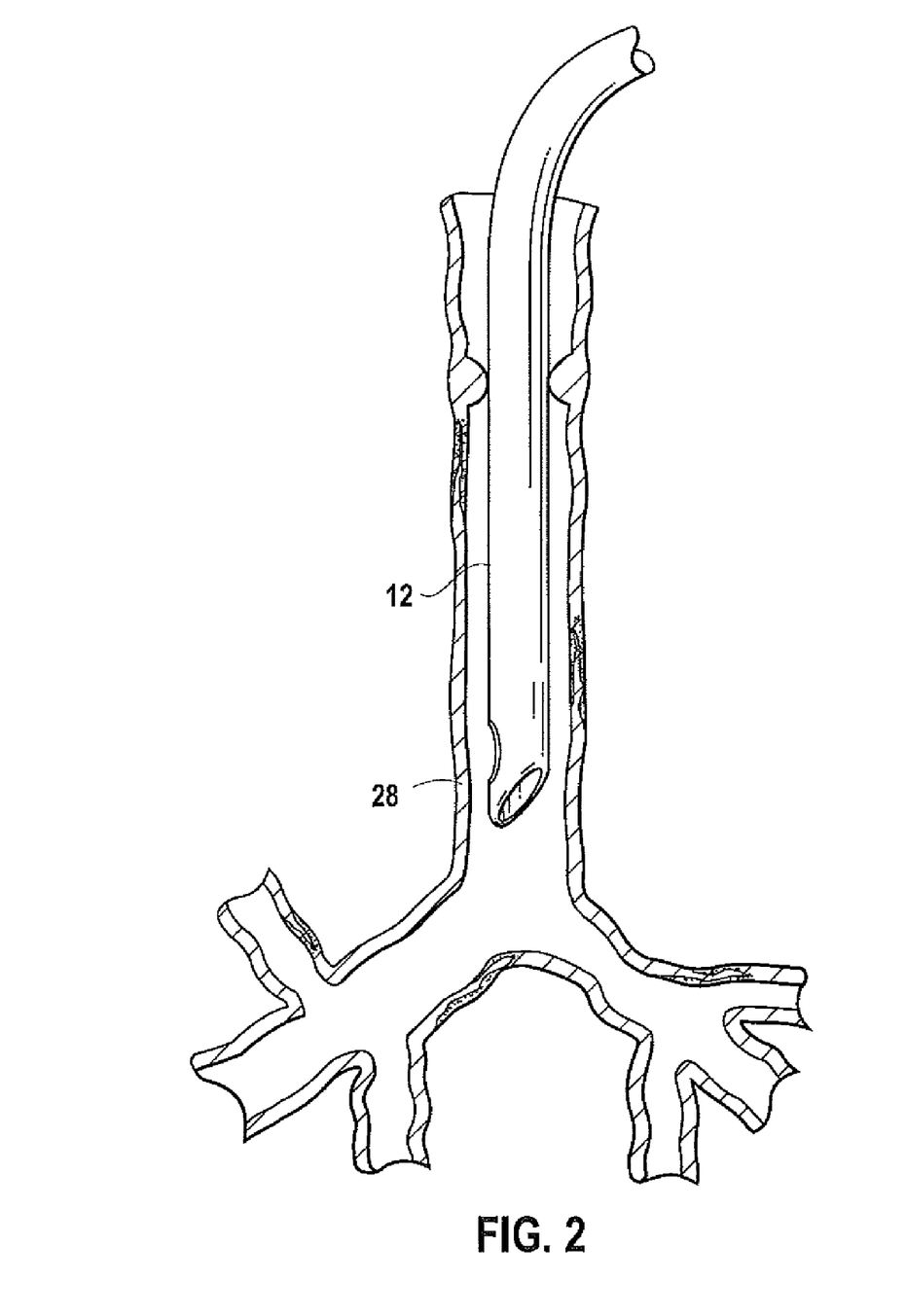
FIG. 2 illustrates an endotracheal tube inserted into a patient's trachea in accordance with an embodiment of the present disclosure.

An example of an endotracheal tube system 10 is depicted in FIG. 1. The system 10 includes an endotracheal tube 12 having a distal end 14 that may be inserted inside the trachea (and sealed against the trachea wall as depicted in FIG. 2). As discussed below, the tube 12 may be constructed of or incorporate material that changes shape, i.e., decreases or increases in size, in response to exposure to light and/or heat. The system 10 also includes an insertion rod 16, e.g., a stent, having energy sources 18 disposed thereon, which may be light and/or heat sources. To power the energy sources 18, a power supply, such as a battery, may be integrated with the energy sources 18. In addition or in lieu of an integrated power supply, the energy sources 18 may have connections for coupling the energy sources 18 to an external power supply.

In operation, the insertion rod 16 may be used to guide the tube 12 into the trachea. For example, the distal end 20 of the rod 16 may be inserted inside the tube 12, and the handle 22 of the rod 16 held by a physician or nurse to guide the tube 12 via the rod 16 into the trachea of the patient. Moreover, the energy sources 18 may be activated or deactivated to expand or contract the outer diameter of the tube 12. In other words, as discussed below, the structural order of the nematic polymer or elastomer of the tube 12 may be promoted or disrupted by exposure to light or heat from the energy sources 18 and, thus, changing the shape of the polymer to increase or decrease the outer diameter of the tube 12. It should be noted that energy sources may be integrated with the tube 12 itself. In one example, a fiber optic wire is integrated with the tube 12 to provide a light source.

In accordance with the present disclosure, the endotracheal tube 12 may be constructed of or incorporate nematic or liquid crystalline polymers or elastomers. As appreciated by one of ordinary skill in the art, the molecules of a nematic polymer or elastomer may be oriented generally parallel as opposed to isotropic. Typically, the molecules of the nematic polymer or elastomer consist of a rigid moiety and one or more flexible parts. The rigid parts (called mesogens) align the molecules in one direction, whereas the flexible parts may provide for elasticity. Thus, nematic polymers have rigid or mesogen structures which induce alignment of the molecules and structural order in the polymer. Depending on the selected nematic polymer and presence of certain additives, such as dyes, exposure of the nematic polymer to light or heat may promote or disrupt the alignment and structural order, resulting in a change in shape of the polymer.

Nematic polymers generally have shape anisotropy, and may order nematically, inducing shape change. Such polymers may be labeled main chain nematic polymers (having mesogens in the backbone of the polymer) or side chain nematic polymers (having pendant mesogens). Exemplary main-chain nematic polymers are given below:

An exemplary side-chain nematic polymer is given below:

Nematic polymers may be crosslinked to form nematic elastomers. Such nematic polymers or elastomers may be sensitive to light or various wavelengths of light. Thus, when exposed to light or to particular wavelength ranges of light or the absence of light, the nematic polymer may change shape (e.g., decrease or increase in size), In certain embodiments, the nematic polymer or elastomer may incorporate dye molecules, such as azobenzene, which may undergo photoisomerization. These polymers may be labeled azo-nematic rod polymers or photochromes. When subjected to light, the dye molecules in these polymers or elastomers may absorb photons and undergo photoisomerization, changing from the trans isomer (a straight structure) to the cis isomer (a bent structure). The increasing presence of the cis isomer (bent rods) may disrupt the nematic order of the polymer or elastomer, making the polymer more isotropic, and thus inducing shape change in the polymer. Below is an example of the isomerization of the dye azobenzene from trans isomers ("straight" molecules) to cis isomers ("bent" molecules), which would disrupt the nematic or structural order of the surrounding nematic elastomer:

In one example, the tube 12 is constructed of a nematic elastomer loaded with a dye (e.g., a green dye) and is exposed to a laser pulse (e.g., a green laser pulse). The elastomer having the green dye absorbs the laser energy, potentially providing for both photo-contraction and differential thermal contraction. In other words, with photo-contraction, the dye photoisomerizes, lowering the nematic order of the elastomer and, thus, contracting the elastomer. Further, absorption of the laser energy may heat the elastomer and provide for thermal contraction.

In another example, the energy source 18 is a light source configured to emit ultraviolet light having a wavelength of about 365 nanometers (nm), in the range of about 330 nm to about 400 nm. The tube 12 has incorporated therein a dye (e.g., azobenzene) that undergoes isomerization (from trans isomers to cis isomers) when exposed to ultraviolet light having a wavelength of about 365 nm in the range of about 330 nm to about 400 nm. The isomerization (photoisomerization) lowers the nematic order of the nematic elastomer of the tube 12, and thus contracting or decreasing the size of the tube 12.

As appreciated by the skilled artisan, the tube 12 constructed of nematic polymers or elastomers may be fabricated in a number of ways. For example, in one embodiment, tube 12 may be manufactured by a blow molding process or extrusion blow molding process. For instance, the tube 12 may also be made by using preextruded tubing and applying heat and pressure appropriately within a molding cavity to achieve the desired shape (blow molding). These tubes can also be formed by extrusion blowmolding, wherein an extruder fed polymer pellets melts the polymer and feeds the molten polymer through a die to form a tube shape. This still molten polymer is then captured in a mold and air pressure is applied to expand the tube out to the walls of the mold, thus achieving the desired shape.

In the extrusion blow molding process, a core or mandrel of the extruder has apertures to admit a gas such as pressurized air or an inert gas like nitrogen, into the medical device in the neighborhood of the tube 12. After a length of medical device has been extruded, a mold clamps the medical device around the mandrel. As gas is admitted to the tube 12 area through the mandrel, the tube 12 expands against the mold. In the alternative, the tube 12 wall may be expanded in a second discrete expansion process following an extrusion or molding process, such as with a shuttle blow molding process. After initial extrusion, the extruded tube 12 will have a generally tubular shape with a substantially uniform wall thickness. It should be noted that a programmable parasin may allow the wall thickness being extruded to be controlled as a function of length. Therefore, the extruded section may have walls of varying thickness. This extruded section may then be blow-molded as described above.

FIG. 2 shows the exemplary endotracheal tube 12 inserted into a patient's trachea. The tube 12 is expanded to form a seat against the tracheal walls 28 and may prevent secretions or other detritus from passing through the trachea into the lungs. It should be noted that the endotracheal tube 12 may be used in conjunction with any suitable medical device. In certain embodiments, the tubes as provided herein may be used in conjunction with a catheter, a feeding tube, an intravenous tube, an endotracheal cuff, a tracheotomy tube, a circuit, an airway accessory, a connector, an adapter, a filter, a humidifier, a nebulizer, or a prosthetic, and the like. The tube 12 may be incorporated into systems that facilitate positive pressure ventilation of a patient, such as a ventilator. Such systems may typically include connective tubing, a gas source, a monitor, and/or a controller. The controller may be a digital controller, a computer, an electromechanical programmable controller, or any other control system.

Figure 3:
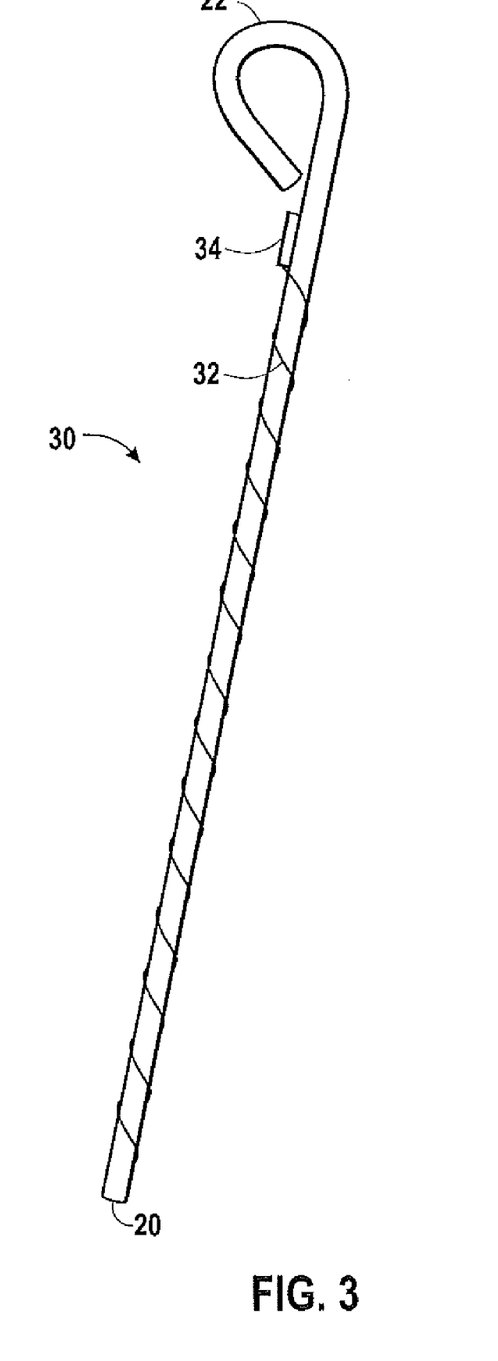
FIG. 3 illustrates an insertion rod in accordance with an embodiment of the present disclosure.

FIG. 3 shows an exemplary insertion rod 30 having a fiber optic wire 32. A connection 34 is provided for coupling the fiber optic wire to a power supply. The fiber optic wire 34 may emit light, exposing the tube 12 (FIGS. 1 and 2) to light or to a particular wavelength of light. The fiber optic wire 34 may also provide heat to the tube 12.

Figure 4:
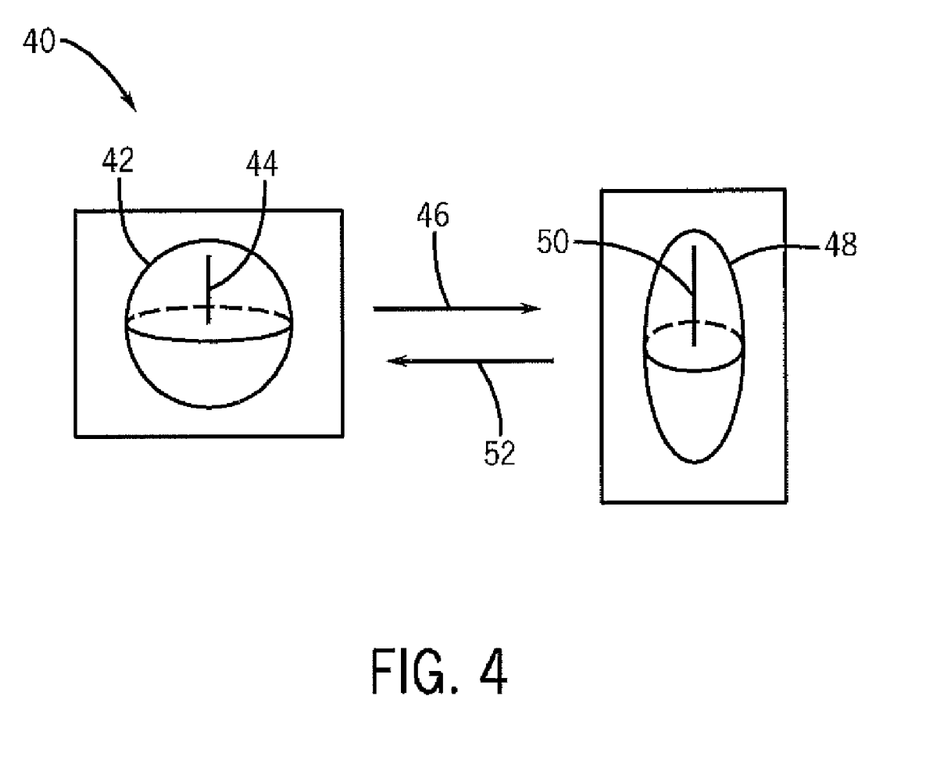
FIG. 4 illustrates a representation of a change in shape of a nematic polymer or elastomer in response to light or heat.

FIG. 4 is a representation 40 of a change in shape of a nematic polymer or elastomer. A polymer having a spherical shape 42 and diameter 44 a change in shape upon the lack of exposure to light or exposure to cooling, as indicated by arrow 46. In this conceptual example, the shape of the polymer may then become a prolate spheroid 48 having a diameter 50 in the longitudinal direction. The polymer may return to the spherical 42 shape upon exposure to heat or light, as indicated by arrow 52.

Nematic or liquid crystalline polymers, and their monomers, may be rodlike (e.g., aromatic polyamides, esters, azomethines, benzobisoxazoles), helical (polypeptides, nucleotides, cellulosics), side-chain mesogenic (e.g., comb polymers), or block copolymers with alternating rigid and flexible units. Polymers exhibiting nematic behavior may be highly aromatic and utilize linear linkages of restricted rotation, e.g., esters, amides, or azomethines. Low molecular weight liquid crystalline (LC) compounds have been known for over one hundred years. However, LC polymers have generally attained prominence only in the last twenty years, owing in part to the discovery of the aramids, such as poly(p-phenylenediphthalamide) (PPD-T), the polyamide from p-phenylenediamine and terephthalic acid, and the commercial development of strong fibers and unique plastics from these materials. Structural features of LC polymers may involve a succession of para-oriented ring structures to give a stiff chain with a high axial ratio (main chain LC polymers), or a rodlike ring containing side chains, e.g., vinyl polymer chains (side chain LC polymers). In one example, a nematic liquid crystal that be polymerized to form a nematic polymer is p-azoxyanisole:

In a calamitic polymer, the mesogen is a rod-like structure composed of two or more aromatic and aliphatic rings connected in one direction. In a discotic polymer, the mesogen is flat-shaped aromatic core that makes molecules stack in one direction. These rod-like and disk-like structures are formed not only by covalent bonds, but also by non-covalent interactions, such as hydrogen bonds, ionic interactions, and metal coordination. Again, structures which define the macromolecular shapes of the assembled molecules may be called mesogens or mesogenic parts.

Figure 5:
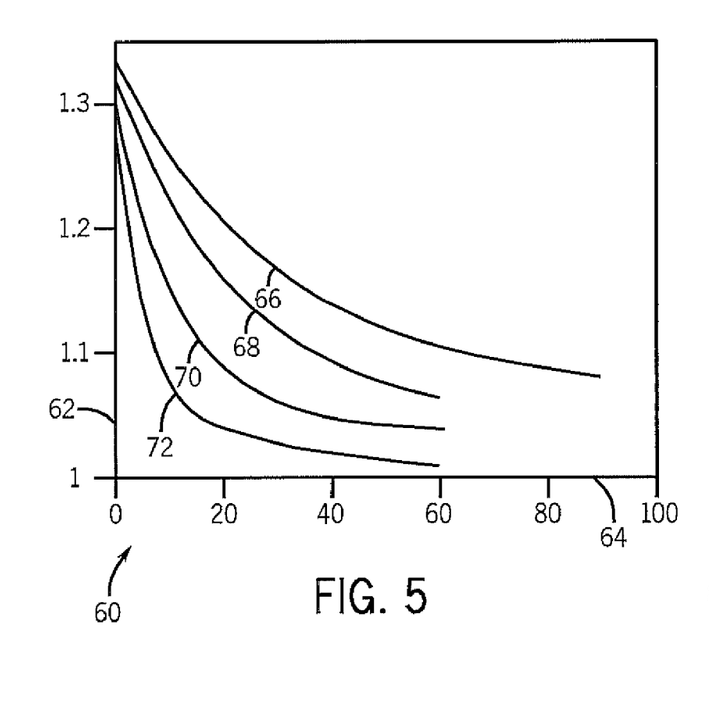
FIG. 5 is a plot of the estimated relative diameter of an endotracheal tube as a function of irradiation time in accordance with an embodiment of the present disclosure.

FIGS. 5-8 provide prophetic examples of the change in diameter of a tracheal tube 12 when exposed to light or heat. These examples are based on tests of exposing strips of nematic elastomers to light and heat, and then measuring the change in length of the strips. FIG. 5 is a prophetic example of a plot 60 of the relative outer diameter ($D/D_0$) 62 of tube 12 versus irradiation time 64 of light in minutes. The four curves 66, 68, 70, and 72 are at respective temperatures of 25° C., 30° C., 35° C. and 40° C. As can be seen from the plot 60, the initial outer diameter, i.e., in the expanded state, is at a factor of about 1.3 greater (or 30% greater) than the outer diameter of a tube in a contracted state. Over time, as the polymer of tube 12 would be exposed to the light, the outer diameter contracts, approaching a factor of 1. Further, the warmer the temperature, the steeper and greater the contraction. Moreover, it should be apparent the tube 12 would expand upon the lack of exposure to light.

Figure 6:
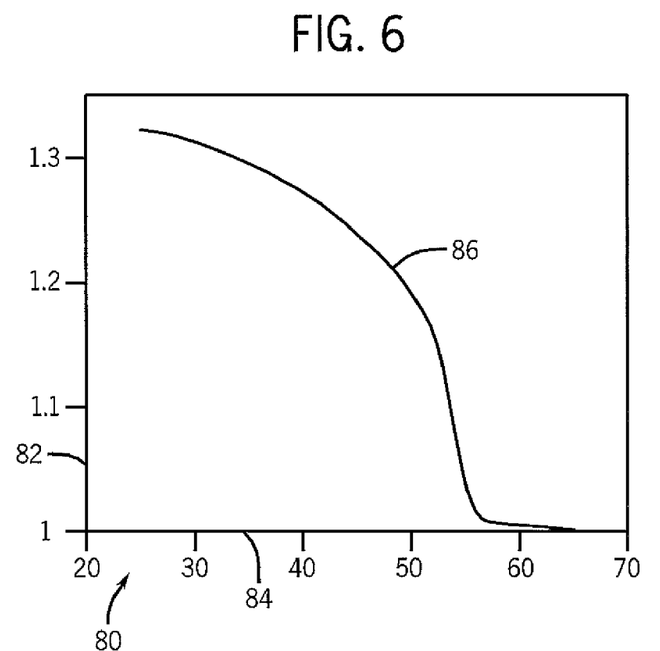
FIG. 6 is a plot of the estimated relative diameter of an endotracheal tube as a function of temperature in accordance with an embodiment of the present disclosure.

FIG. 6 is a prophetic example of a plot 80 of the relative outer diameter 82 of a tube 12 versus temperature 84 in degrees Celsius The curve 86 has a flatter slope at lower temperatures and reaches a steeper slope at approximately 50-60° C. where it approaches a factor of 1 at 60° C. Thus, in this illustrated embodiment, the tube 12 would contract upon exposure to heat. Also, it should be apparent that the tube would expand upon exposure to cooling.

Figure 7:
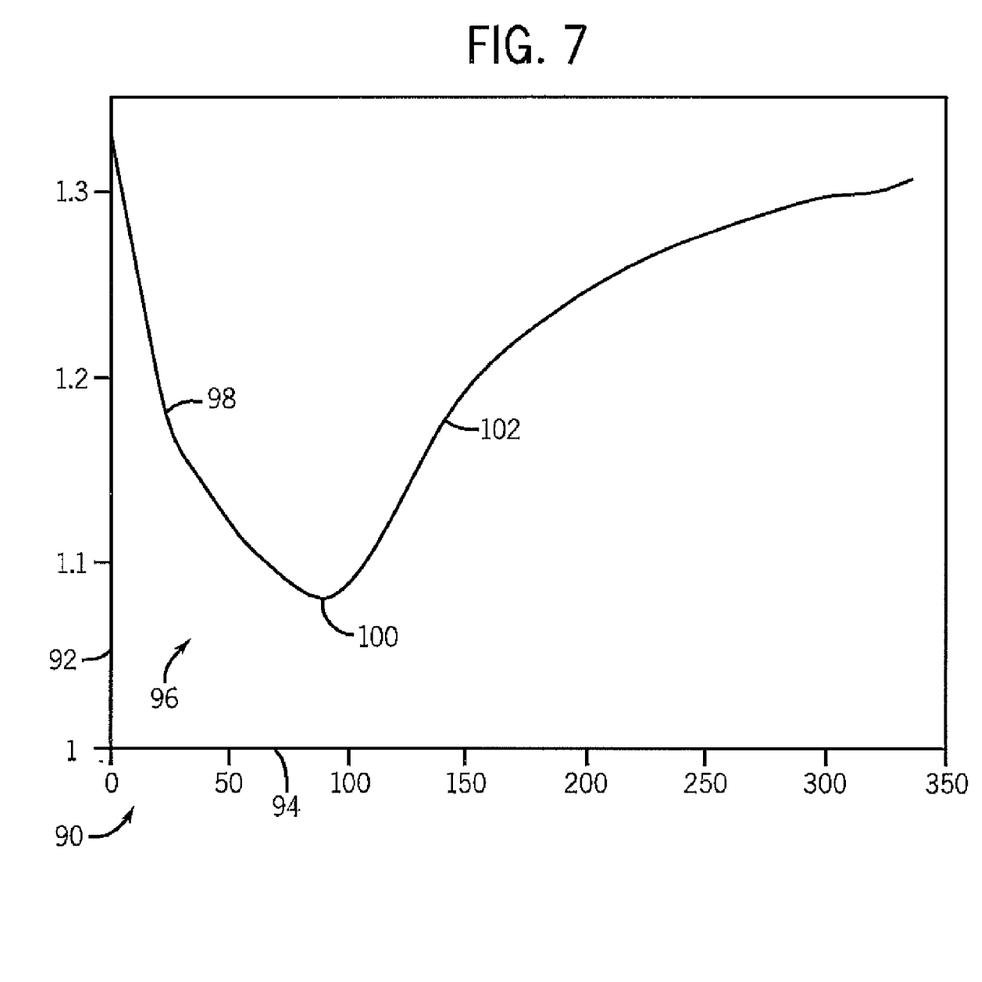
FIG. 7 is a plot of the estimated diameter of an endotracheal tube as a function of exposure to light in accordance with an embodiment of the present disclosure.

FIG. 7 is a prophetic example of a plot 90 of the relative outer diameter 92 of a tube 12 versus irradiation time 94 in minutes. The curve 96 has a decreasing slope 98 upon exposure to light. In this example, at about 90 minutes, as indicated by reference numeral 100, the light source is turned off and the tube is exposed to darkness. Thus, as indicated by reference numeral 102, the tube 12 would begin to expand in the absence of light.

Figure 8:
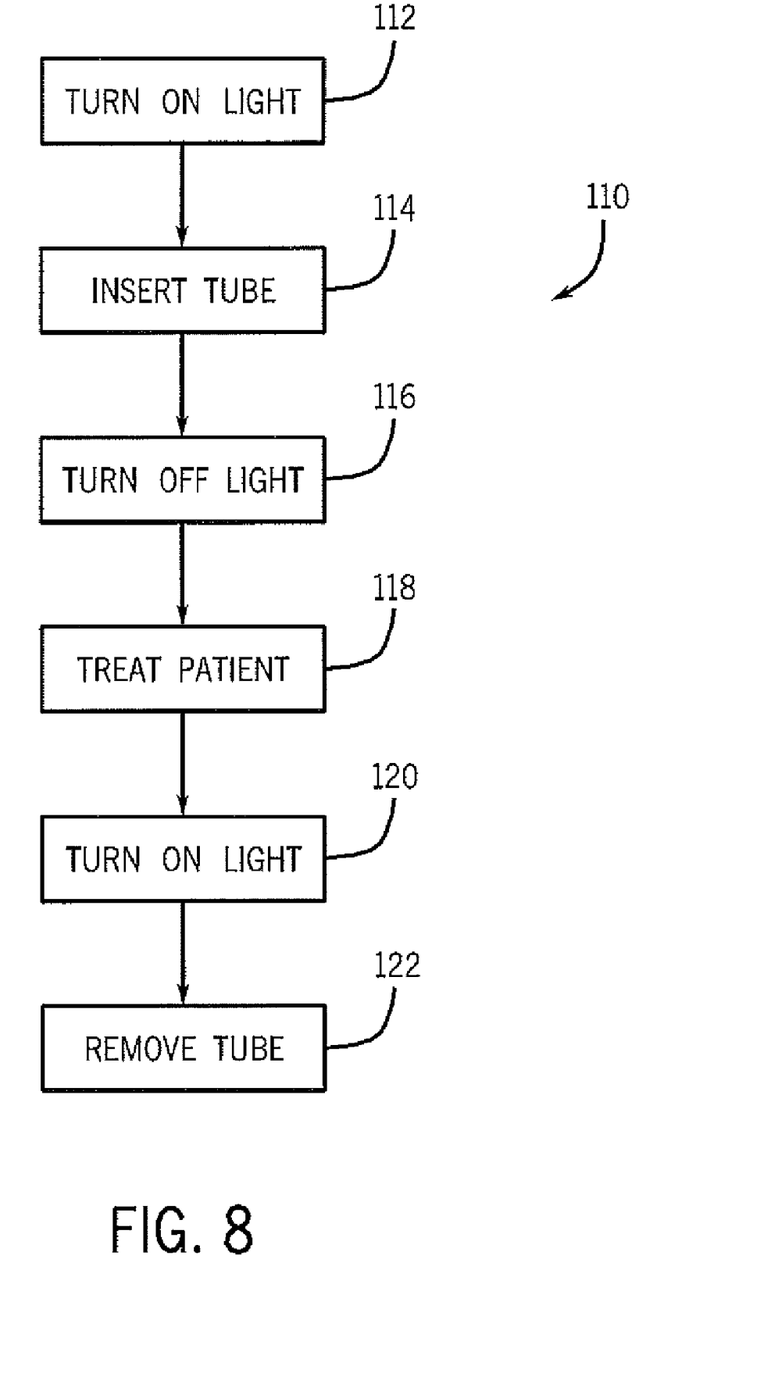
FIG. 8 is a block diagram of a method for using an endotracheal tube in accordance with an embodiment of the present disclosure.

FIGS. 8-11 depict methods for treating a patient with an endotracheal tube 12. FIG. 8 depicts a method 110 for a tube 12 constructed of a nematic polymer or elastomer that contracts upon exposure to light. Initially, the light source is turned on, as indicated by block 112. Thus, the tube 12 contracts when exposed to the light. The tube 12 is then inserted into the patient (e.g., into the trachea) and the light is turned off, as indicated by blocks 114 and 116, respectively. When the light is turned off the tube 12 may then expand and seal against the patient's passageway, reducing the amount of material bypassing the tube and facilitating the inflow of materials through the tube 12 into the patient. Lastly, the light is then turned on (block 120) to contract the tube, and the tube is removed (block 122) from the patient. The light may then be turned off after removal of the tube 12 from the patient.

Figure 9:
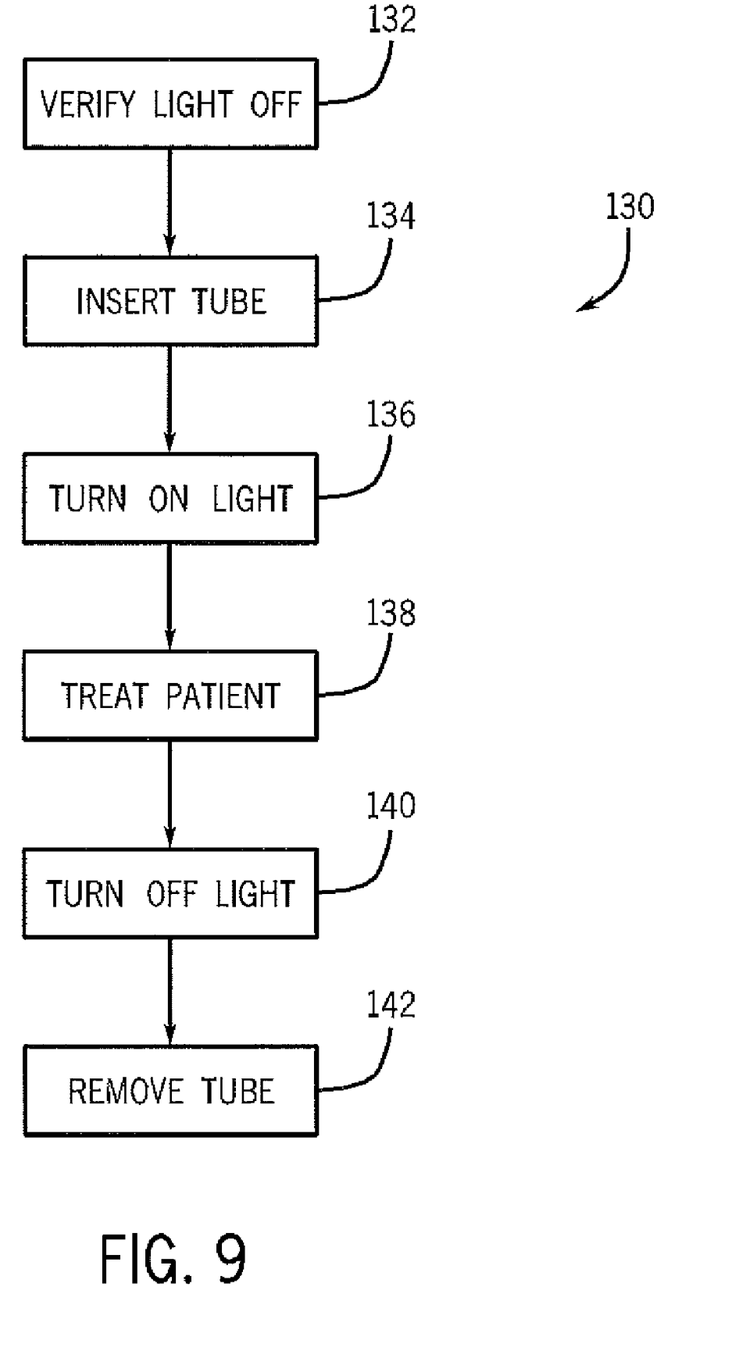
FIG. 9 is a block diagram of a method for using an endotracheal tube in accordance with an embodiment of the present disclosure.

FIG. 9 depicts a method 130 for use with a tube 12 constructed of a material, e.g., nematic polymer or elastomer, that expands upon exposure to light or to a specific wavelength range of light. In operation, the user may verify that the light source is off (block 132), such that the tube is in its contracted state. The tube 12 may then be inserted (block 134) into the patient and the light turned on (block 136) to expand the tube and seal the tube against the patient's passageway (e.g., trachea). The patient is then treated with the injection of oxygen or medications, for example, via the expanded and sealed tube 12, as indicated by reference numeral 138. The light is then turned off (block 140) and the tube 12 removed (block 142) from the patient. It should be noted that the methods 110 and 130 depicted in FIGS. 8 and 9 may be changed for alternate embodiments, for example, such that turning the light on or off may instead be adjusting the wavelength of the light emitted.

Figure 10:
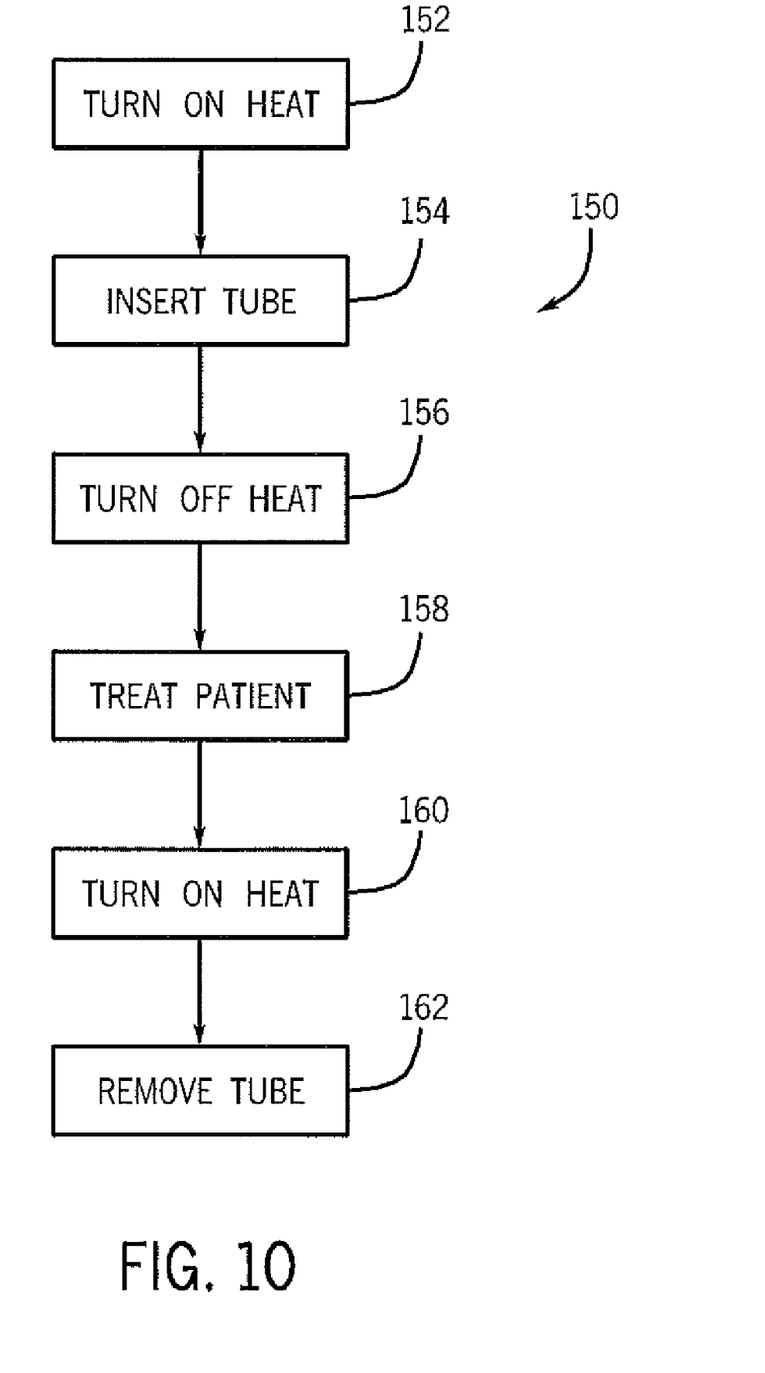
FIG. 10 is a block diagram of a method for using an endotracheal tube in accordance with an embodiment of the present disclosure.

FIG. 10 depicts a method 10 for using a tube 12 constructed of material that contracts when exposed to heat. In this example, the heat is turned on (block 152) to contract the tube and the tube is inserted (block 154) into the patient. The heat is then turned off (block 156) to expand the tube and seal the tube against the interior surface of the patient's passageway, as indicated by reference numeral 156. It should be apparent that in block 156, in addition to turning off the heat, the tube 12 may be exposed to active cooling to expand the tube. The patient is then treated (block 158) with the tube 12. The heat is turned on (block 160) to contract the tube, and the tube is removed (block 162) from the patient.

Figure 11:
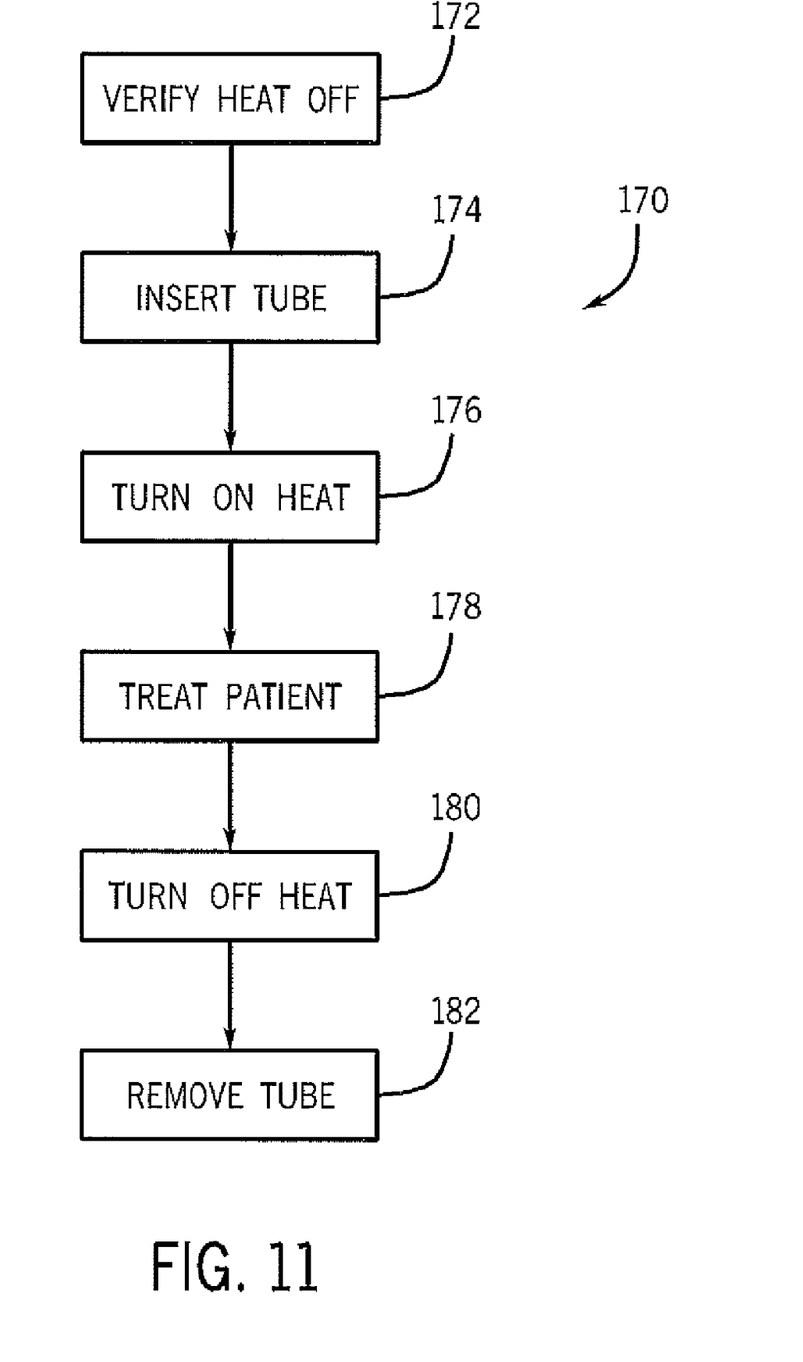
FIG. 11 is a block diagram of a method for using an endotracheal tube in accordance with an embodiment of the present disclosure.

FIG. 11 depicts a method 170 for using a tube 12 that expands when exposed to heat. Initially, an operator may verify that the heat source is turned off (block 172) prior to inserting the tube into the patient. With the ambient temperature tube (or cold tube) the tube is inserted into the patient, as indicated by reference numeral 174. Again, the tube is generally inserted into a passageway, such as the trachea, of the patient. The heat is turned on (block 176) to seat the tube against the surface of the passageway and the patient is then treated, as indicated by reference numerals 176 and 178, respectively. Upon completion of treatment, the heat source is turned off (block 180) and the tube is removed (block 182) from the patient.

Figure 12:
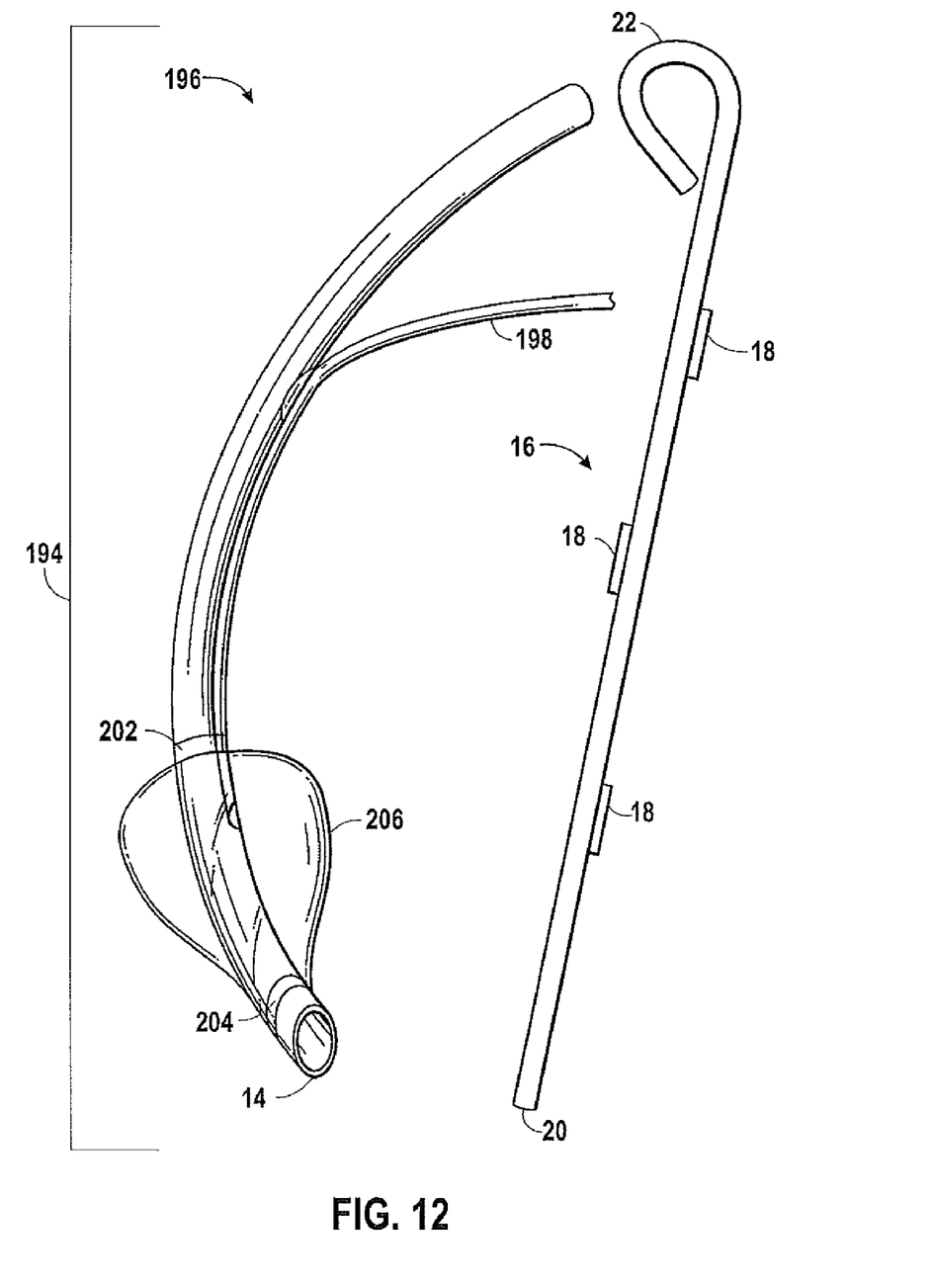
FIG. 12 illustrates an endotracheal tube system in accordance with an embodiment of the present disclosure.

FIG. 12 depicts a endotracheal tube system 194 including a cuffed endotracheal tube 196 having an inflatable cuff 206 that may be inflated to form a seal against the trachea wall 28 (see FIG. 2). The tube 196 including the cuff 206 may be constructed of a nematic polymer or elastomer to facilitate expansion or contraction when the tube 196 and/or cuff 206 is exposed to light or heat. Moreover, the cuff 206 may be maintained in an inflated or expanded state (e.g., constructed of silicon foam or other material), and the tube 196 characteristics allowing insertion with such a cuff 206 and sealing after applying (or removing) heat, light, etc.

It should be noted that the cuff 206 is disposed on an endotracheal tube 196 that is suitably sized and shaped to be inserted into a patient and allow the passage of air through the endotracheal tube 196. Typically, the cuff 206 is disposed, adhesively or otherwise, towards the distal end 14 of the endotracheal tube 196. The cuff 206 may be inflated and deflated via a lumen 198 in communication with the cuff 206, typically through a hole or notch in the lumen 198. As mentioned above, however, the cuff 206 may be maintained in an expanded state, and further expanded via exposure to an energy source, such as light or heat. In other embodiments, the cuff 206 may generally have an amorphous, or irregular, shape in the uninflated state and may assume a spherical or tapered shape when inflated. The cuff 198 has a proximal opening 202 and a distal opening 204 formed in the cuff walls sized to accommodate the endotracheal tube 196. The proximal opening 202, located closer to the "machine end" of the tube 196, and a distal opening 204, located closer to the "patient end" of the tube 196, are typically used to mount the cuff 206 to the tube 196.

While the disclosure may be susceptible to various modifications and alternative forms, specific embodiments have been shown by way of example in the drawings and have been described in detail herein. However, it should be understood that the disclosure is not intended to be limited to the particular forms disclosed. Rather, the disclosure is to cover all modifications, equivalents, and alternatives falling within the spirit and scope of the disclosure as defined by the following appended claims.

What is claimed is:

1. A tracheal tube comprising a nematic polymer or nematic elastomer, or a combination thereof, wherein an outer diameter of the tracheal tube changes in size in response to exposure of the tracheal tube to a light source or to a heat source, or a combination thereof.

2. The tracheal tube of claim 1, wherein the tracheal tube comprises at least the light source or the heat source, or a combination thereof.

3. The tracheal tube of claim 2, wherein the light source comprises a fiber optic wire.

4. The tracheal tube of claim 2, wherein the light source comprises the heat source.

5. The tracheal tube of claim 1, wherein the change in size comprises an increase in size of the outer diameter of the tracheal tube.

6. The tracheal tube of claim 1, wherein the change in size comprises a decrease in size of the outer diameter of the tracheal tube.

7. The tracheal tube of claim 1, wherein at least the nematic polymer or the nematic elastomer comprises a polymer of the monomer liquid-crystal p-azoxyanisole, and wherein the monomer liquid-crystal p-asoxynisole comprises the structure:

8. The tracheal tube of claim 1, wherein at least the nematic polymer or the nematic elastomer comprise a side-chain nematic polymer comprising pendant mesogens and having the structure:

wherein n is at least 10.

9. A tracheal tube comprising:

a nematic polymer; and a dye that undergoes isomerization upon exposure to a light source or a heat source, or a combination thereof, wherein isomerization of the dye disrupts a nematic order of the nematic polymer.

10. The tracheal tube of claim 9, wherein the disruption of the nematic order due to isomerization of the dye contracts the diameter of the tube.

11. The tracheal tube of claim 9, wherein the nematic polymer comprises a main chain nematic polymer or a side chain nematic polymer, or a combination thereof.

12. The tracheal tube of claim 9, wherein at the nematic polymer is crosslinked to form a nematic elastomer, and where the tracheal tube comprises the nematic elastomer.

13. The tracheal tube of claim 9, wherein isomerization of the dye comprises isomerizing trans isomer molecules of the dye to cis isomer molecules of the dye.

14. The tracheal tube of claim 9, wherein the dye comprises azobenzene.

15. The tracheal tube of claim 14, wherein isomerization comprises transforming trans isomers of the azobenzene to cis isomers of the azobenzene according to following the structures:

16. The tracheal tube of claim 9, wherein the light source comprises a source of ultraviolet light, and the nematic polymer undergoes isomerization upon exposure to the ultraviolet light.

17. A tracheal tube system comprising:
an energy source; and
a tracheal tube comprising a nematic polymer or nematic elastomer, or a combination thereof, wherein an outer diameter of the tracheal tube changes in size in response to exposure to the energy source when the energy source is active.

18. The tracheal tube system of claim 17, wherein the energy source comprises a light source or heat source, or a combination thereof.

19. The tracheal tube system of claim 17, wherein the energy source is integrated with the tracheal tube.

20. The tracheal tube system of claim 17, comprising an insertion rod, wherein the energy source is disposed on the insertion rod.

\* \* \* \* \*